(12) United States Patent
Shemesh et al.

(10) Patent No.: US 10,856,961 B2
(45) Date of Patent: Dec. 8, 2020

(54) INTRAVASCULAR DEVICES AND DELIVERY SYSTEMS AND USES THEREOF

(71) Applicant: Keystone Heart Ltd., Caesarea (IL)

(72) Inventors: Tzeela Mikovsky Shemesh, Ramat Gan (IL); Moran Gera, Kohav Yair (IL); Amit Ashkenazi, Haifa (IL)

(73) Assignee: Keystone Heart, Ltd., Ceasarea (IL)

( * ) Notice: Subject to any disclaimer, the term of this patent is extended or adjusted under 35 U.S.C. 154(b) by 94 days.

(21) Appl. No.: 15/543,901

(22) PCT Filed: Jan. 20, 2016

(86) PCT No.: PCT/IB2016/000192
§ 371 (c)(1),
(2) Date: Jul. 14, 2017

(87) PCT Pub. No.: WO2016/116816
PCT Pub. Date: Jul. 28, 2016

(65) Prior Publication Data
US 2018/0008392 A1    Jan. 11, 2018
US 2018/0177580 A9    Jun. 28, 2018

Related U.S. Application Data

(60) Provisional application No. 62/105,493, filed on Jan. 20, 2015, provisional application No. 62/144,799, filed on Apr. 8, 2015.

(51) Int. Cl.
*A61F 2/01*    (2006.01)
(52) U.S. Cl.
CPC ............... *A61F 2/01* (2013.01); *A61F 2/011* (2020.05); *A61F 2002/016* (2013.01);
(Continued)

(58) Field of Classification Search
CPC .......................... A61F 2/01; A61F 2002/011; A61F 2002/016; A61F 2230/0008;
(Continued)

(56) References Cited

U.S. PATENT DOCUMENTS

2009/0088780 A1    4/2009    Parodi et al.
2013/0131714 A1    5/2013    Wang et al.
(Continued)

FOREIGN PATENT DOCUMENTS

EP              2732794 A1    5/2014
WO    WO 2014/032038 A1    2/2014

OTHER PUBLICATIONS

WIPO, U.S. International Search Authority, International Search Report and Written Opinion dated Jul. 27, 2016 in International Patent Application No. PCT/IB2016/000192, 8 pages.
(Continued)

*Primary Examiner* — George J Ulsh
(74) *Attorney, Agent, or Firm* — Inskeep IP Group, Inc.

(57) ABSTRACT

In general, the invention features an intravascular device, a delivery system, and methods for filtering or deflecting emboli or other large objects from entering a protected secondary vessel or vessels The intravascular device of the invention may prevent passage of a particle in a blood vessel from passing through a filter supported by a frame, upper and lower stabilizers, and a wire. The wire may be used to stabilize the device upon its deployment and installation within a blood vessel. Further, in some embodiments, the invention features a delivery system and methods for introduction of the device into a blood vessel.

6 Claims, 11 Drawing Sheets

(52) U.S. Cl.
 CPC . *A61F 2002/018* (2013.01); *A61F 2230/0008* (2013.01); *A61F 2230/0019* (2013.01); *A61F 2230/0095* (2013.01)

(58) Field of Classification Search
 CPC ...... A61F 2230/0019; A61F 2230/0095; A61F 2002/018
 See application file for complete search history.

(56) References Cited

U.S. PATENT DOCUMENTS

| | | |
|---|---|---|
| 2013/0218194 A1 | 8/2013 | Jonsson |
| 2014/0074152 A1 | 3/2014 | Shezifi et al. |
| 2014/0172006 A1 | 6/2014 | Stack et al. |
| 2014/0243881 A1 | 8/2014 | Less et al. |
| 2016/0100928 A1* | 4/2016 | Lees ...................... A61F 2/013 606/200 |
| 2016/0324621 A1* | 11/2016 | Shezifi ..................... A61F 2/01 |

OTHER PUBLICATIONS

European Patent Office, Supplemental Search Report dated Jun. 7, 2018 in European Patent Application No. 16739839, 2 pages.
European Patent Office, Opinion dated Jun. 7, 2018 in European Patent Application No. 16739839, 4 pages.
Japan Patent Office, Examiner's Report dated Oct. 29, 2019 in Japanese Patent Application No. 2017-555859, 7 pages.

* cited by examiner

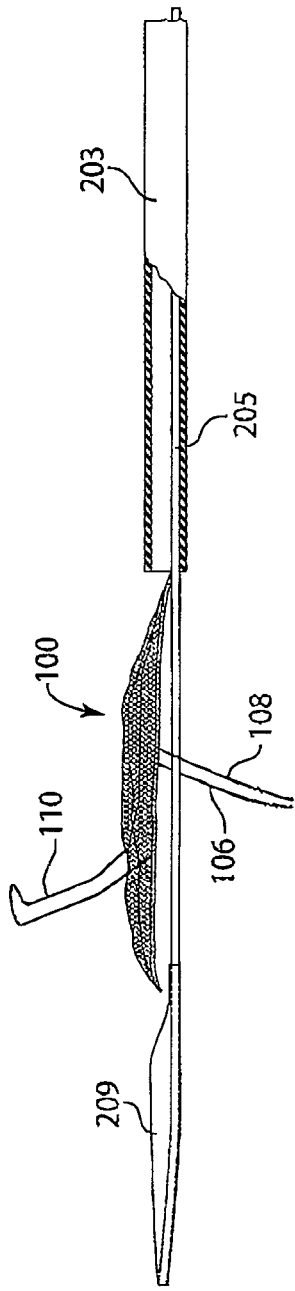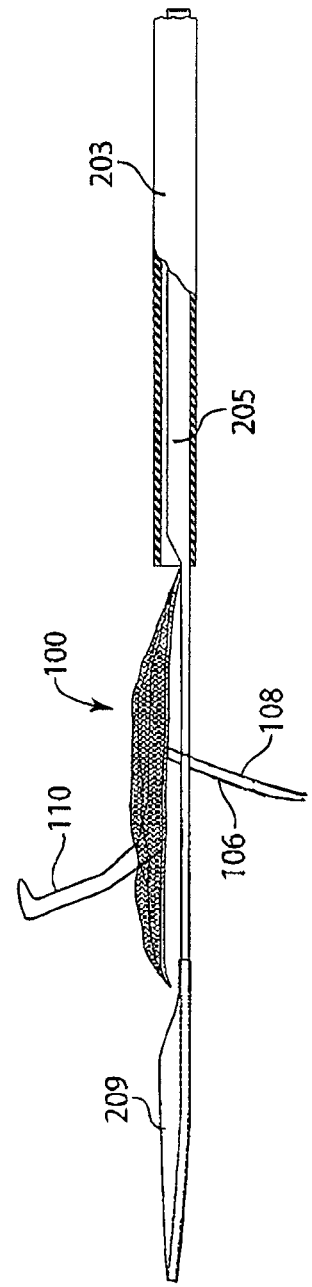
Fig. 5A
Fig. 5B

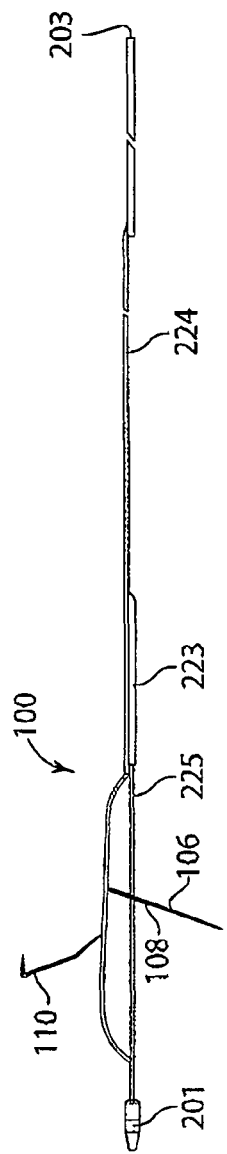
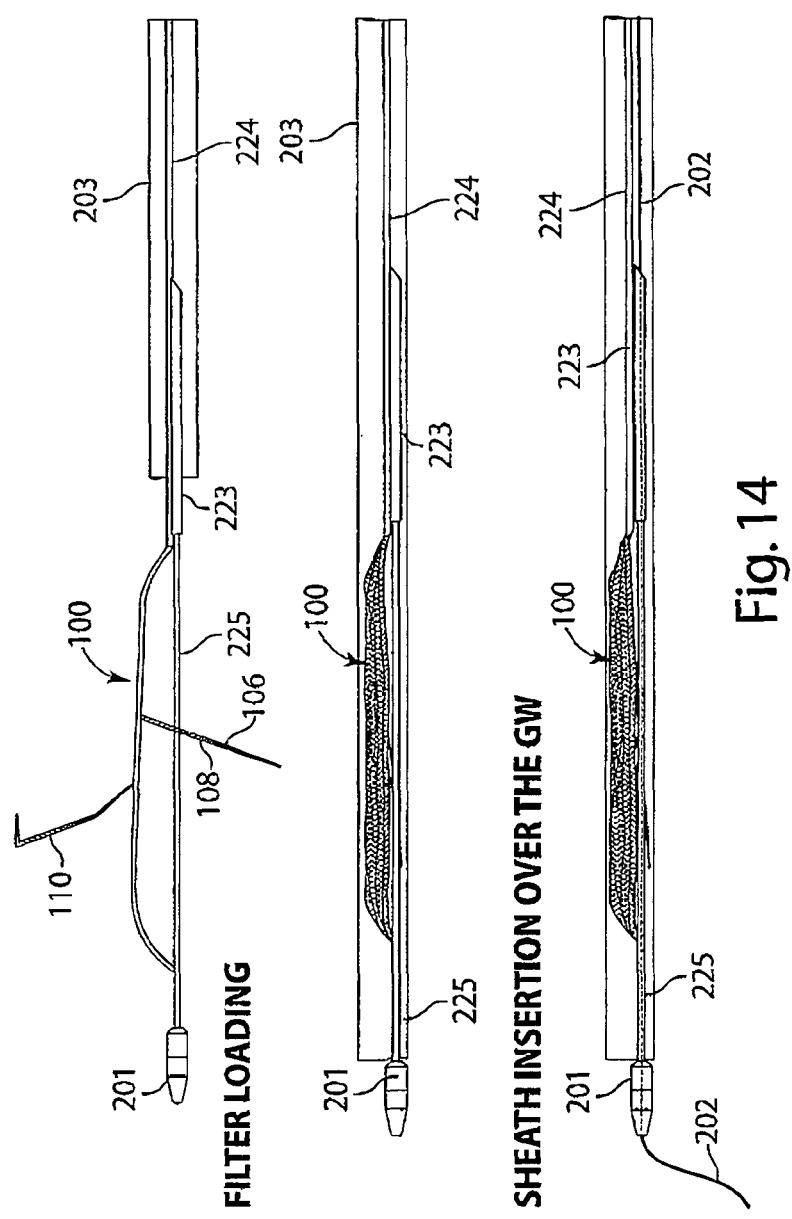
Fig. 13
FILTER LOADING
SHEATH INSERTION OVER THE GW
Fig. 14

INTRAVASCULAR DEVICES AND DELIVERY SYSTEMS AND USES THEREOF

RELATED APPLICATIONS

This application is the U.S. National Phase of and claims priority to International Patent Application No. PCT/IB2016/000192, International Filing Date Jan. 20, 2016, entitled Intravascular Devices And Delivery Systems And Uses Thereof, which claims benefit of U.S. Provisional Application Ser. No. 62/105,493 filed Jan. 20, 2015 entitled Intravascular Devices And Delivery Systems And Uses Thereof, and U.S. Provisional Application Ser. No. 62/144,799 filed Apr. 8, 2015 entitled Intravascular Devices And Delivery Systems And Uses Thereof, all of which are incorporated herein by reference in their entireties.

FIELD OF THE INVENTION

The invention relates to intravascular devices, systems, and methods for deflecting emboli in an aorta to prevent emboli from entering arteries, for example, arteries that lead to the brain.

BACKGROUND OF THE INVENTION

Devices such as vascular filters or other devices may be inserted into a blood vessel prior to or during a procedure or at another time. Such devices may be inserted by way of a catheter that may be passed through a vein or artery, and into, for example, an aorta or other vessel where the device may be released from the catheter and deployed. The device may filter, deflect, or block emboli or other objects from entering into a blood supply that feeds the brain.

SUMMARY OF THE INVENTION

In a first aspect, the invention features an intravascular device for deflecting particles, e.g., emboli, including, a substantially planar frame, e.g., having a length between about 80 mm and 90 mm and a width from about 20 mm to 35 mm; an embolic filter attached to and extending the length of the frame; an upper stabilizer above the horizontal plane of the filter; a lower stabilizer below the horizontal plane of the filter; where one of the upper or lower stabilizer includes a wire configured to run along a horizontal plane of the filter and exert a force on the frame and/or the filter when deployed in an aorta of a subject. The frame of the device may define the shape of the filter and is typically sized and shaped to be held in contact with both an ascending and a descending aorta. An upper stabilizer of the device may extend upward from the horizontal plane of the filter to contact a medial surface of an innominate artery. A lower stabilizer of the device may extend downward from the horizontal plane of the filter to contact a medial surface of the aorta. A device may include multiple upper and/or lower stabilizers.

In one embodiment, the wire is a tether made from a polymeric material, a metal, or any combination thereof, and has a diameter, e.g., of less than 2 mm. A tether may include flushing segments to allow fluid, e.g., saline, to be released from the inner chamber of the tether. The tether may include a lumen via which the intravascular device is attached. For example, a wire may extend through this lumen and attach to or be integral with the intravascular device. In such embodiments, this lumen may be substantially filled by the wire. In additional embodiments, the tether may include a lumen to allow passage of a guide wire. Alternately, the tether may include separate lumens for attachment of the intravascular device, passage of a guide wire, or delivery or removal of fluids. The lumen for the guide wire preferably does not extend the length of the tether and instead is located at the distal end of the tether, e.g., below a lumen used to attached the intravascular device. Preferably, the lumen for a guide wire is longer than the length of the intravascular device. The lumen for the guide wire may be from 70 mm to 160 mm. In such embodiments, a transverse dimension of the tether is preferably larger at the distal end of the tether, where the lumen is located, relative to the proximal end. The tether may be passed over the guide wire via the lumen to advance the device through a delivery system. The guide wire may also be used to support the device when deployed in an aorta of a subject, e.g., by applying a force to the inner walls of the lumen of the tether. The stiffness of the guide wire may vary along its length to produce a desired force on an inner wall of the lumen of the tether. For example, one portion of the guide wire may be less stiff and present in the lumen during deployment and/or positioning. During use, the guide wire may be advanced or retracted to place a stiffer portion in the lumen, which can be used to exert a force on the walls of the lumen. In some embodiments, the tether may be attached to a protected lip at its distal end. The protected lip may be a dilator tip that may be inflated to expand a blood vessel during, e.g., introduction of the device into the aorta.

In embodiments where the lower stabilizer includes the tether, the dilator tip may be inflated with a fluid, e.g., air or saline, or a guide wire may exert pressure to provide lift to the device when deployed within an aortic arch. In embodiments where the upper stabilizer includes the tether, the dilator tip may be inflated with a fluid, e.g., air or saline, or a guide wire may exert a force along the frame and filter of the device to push it in a direction of an ascending aorta when deployed in the aortic arch of a subject. In such embodiments, the dilator tip may contact a medial surface of an innominate artery. The tether and the dilator tip may have equal rigidity, or unequal rigidity, in which the tether is more rigid than the dilator tip or the dilator tip is more rigid than the tether.

In certain embodiments, the filter has a radius of curvature of no less than 80 mm (e.g., no less than 90 mm, 100 mm, 110 mm, 120 mm, 130 mm, 140 mm, or 150 mm).

In certain embodiments, the device includes the tether as a lower stabilizer and a single upper stabilizer, e.g., that contacts a medial surface of an innominate artery. In such embodiments, further lower stabilizers may also be present, e.g., two further lower stabilizers attached to opposite sides of the frame and extending downward from the horizontal plane of the filter, e.g., to contact a medial surface of the aorta. In other embodiments, the device includes the tether as an upper stabilizer and two lower stabilizers, e.g., two further lower stabilizers attached to opposite sides of the frame and extending downward from the horizontal plane of the filter, e.g., to contact a medial surface of the aorta. In such embodiments, a further upper stabilizer may also be present, e.g., that contacts a medial surface of an innominate artery.

In a second aspect, the invention features a delivery system including a device of the invention and an introducer sheath having a lumen for introduction of the device to an aorta of a subject. The introducer sheath may be made of a braided or coiled material and may further include a Y-connector with three ports to allow for introduction of devices into a lumen of the sheath. The introducer sheath may have a size in the range of 6 F-10 F (e.g., 6 F, 7 F, 8 F, 9 F, or 10

F). In some embodiments, the delivery system includes a second guide wire. The delivery system may further include a pigtail catheter, e.g., a 1 F, 2 F, 3 F, 4 F, 5 F, and 6 F pigtail catheter, e.g., which may have a blunted tip and is delivered over the second guide wire. In additional embodiments, the delivery system includes a deflector made from an expandable or spread material. The deflector may include a frame or may be frameless.

In an embodiment of the delivery system, the device is loaded into the introducer sheath, e.g., with the frame, upper stabilizer, and/or lower stabilizer compressed to fit within the lumen. In embodiments where the device includes a protected lip, the protected lip may be positioned distal to the introducer sheath and have a smaller diameter than the introducer sheath. When loaded into the introducer sheath, the device may be compressed within the introducer sheath and positioned behind any protected lip. Upon retraction of the introducer sheath relative to the intravascular device, the device may be expanded and deployed into an aorta of a subject. In other embodiments, a pigtail catheter, a tether, and the intravascular device are loaded into a single lumen of the introducer sheath. In such embodiments, the tether may include a lumen for attachment of the intravascular device and/or a lumen for a guide wire, e.g., one located at the distal end of the tether and not extending the length of the tether. The tether having a guide wire lumen at the distal end may be sized so that deployment of the distal end from the introducer sheath frees volume to allow for passage of other tools, e.g., a pigtail catheter through the introducer sheath. In another embodiment, the intravascular device and the tether are loaded into a first lumen of a dual lumen introducer sheath, and the pigtail catheter is loaded into a second lumen of the dual lumen introducer sheath.

In a third aspect, the invention features a method of introducing the device or delivery system into a subject by inserting the device contained within an introducer sheath into a blood vessel, e.g., aorta, of the subject and retracting the sheath relative to the device at a desired location in the blood vessel, thereby deploying the device into an aortic arch of a subject. When deployed, an upper stabilizer may extend upward from the horizontal plane of the filter and contact a medial surface of an innominate artery, and/or a lower stabilizer may extend downward from the horizontal plane of the device and contact a medial surface of the wall of the aorta. In some embodiments, the device of the invention is passed through an introducer sheath by a tether, e.g., one including a lumen for attachment of the intravascular device and/or a lumen for a guide wire, advanced over a guide wire. In other embodiments, a pigtail catheter is introduced through the introducer sheath and is inserted over a second guide wire. The device and delivery system are preferably over the wire systems, where a guide wire is introduced to the desired location and the device and delivery system are advanced over the guide wire to the desired location. The guide wire may then remain in the device or be removed after deployment. Preferably, the device and delivery system are introduced via a peripheral artery, e.g., femoral artery.

In another aspect, the invention features a catheter having a lumen for a guide wire located at the distal end, where the lumen does not extend the length of the catheter. A transverse dimension of the catheter is preferably larger at the distal end, where the lumen is located, relative to the proximal end. The sizes, shapes, and materials described herein for tethers may also be employed in conjunction with a catheter of the invention. The catheter may be attached to any tool for use intravascularly, e.g., one including a filter for emboli, an electrode, a cutting element, an imaging element, or a balloon, or may include a mechanism for attachment to such a tool. Preferably, the lumen for a guide wire is longer than the length of any attached intravascular tool. The lumen for the guide wire may be from 70 mm to 160 mm. In some embodiments, the catheter may be attached to a protected lip at its distal end. The protected lip may be a dilator tip that may be inflated to expand a blood vessel during, e.g., introduction of the device into the aorta.

As used herein, the term "wire" refers to any elongated structure (e.g., cords, fibers, yarns, filaments, cables, and threads) fabricated from any non-degradable material (e.g., polycarbonate, polytetrafluorothylene (PTFE), expanded polytetrafluorothylene (ePTFE), polyvinylidene fluoride (PVDF), polypropylene, porous urethane, metal, Nitinol, fluropolymers (e.g., Teflon®), cobalt chromium alloys (CoCr), and para-aramid (Kevlar®), or textile (e.g., nylon, polyester (e.g., Dacron®), or silk).

As used herein, the term "pigtail catheter" refers to a surgical device that is used to introduce radio-opaque contrast.

BRIEF DESCRIPTION OF THE DRAWINGS

FIG. 3A is a diagram of a device having a tether attached to a dilator tip that functions as a lower stabilizer of the intravascular device, and FIG. 3B is a representation of the device of FIG. 3A deployed in an aortic arch, in accordance with an embodiment of the invention. FIG. 3C is a diagram of a device with a tether attached to a dilator tip that functions as an upper stabilizer of an intravascular device (left), and a delivery system with a dilator tip connected to a tether that functions as an upper stabilizer of an intravascular device (right), in accordance with an embodiment of the invention. FIG. 3D is a representation of a device with a dilator tip functioning as an upper stabilizer deployed in the aortic arch, in accordance with an embodiment of the invention.

FIG. 5A is a diagram of a delivery system with a low-profile tether having uniform rigidity, in accordance with an embodiment of the invention.

FIG. 5B is a diagram of a delivery system with a tether having variable rigidity, in accordance with an embodiment of the invention.

FIG. 13 is a diagram of a tether with a first lumen for attachment of the intravascular device and a second lumen for a guide wire to pass beneath the intravascular device, in accordance with an embodiment of the invention.

FIG. 14 is a diagram of an intravascular device attached to a tether being loaded into a lumen of an introducer sheath by a delivery system, in accordance with an embodiment of the invention.

DETAILED DESCRIPTION OF THE INVENTION

Figure 1A:
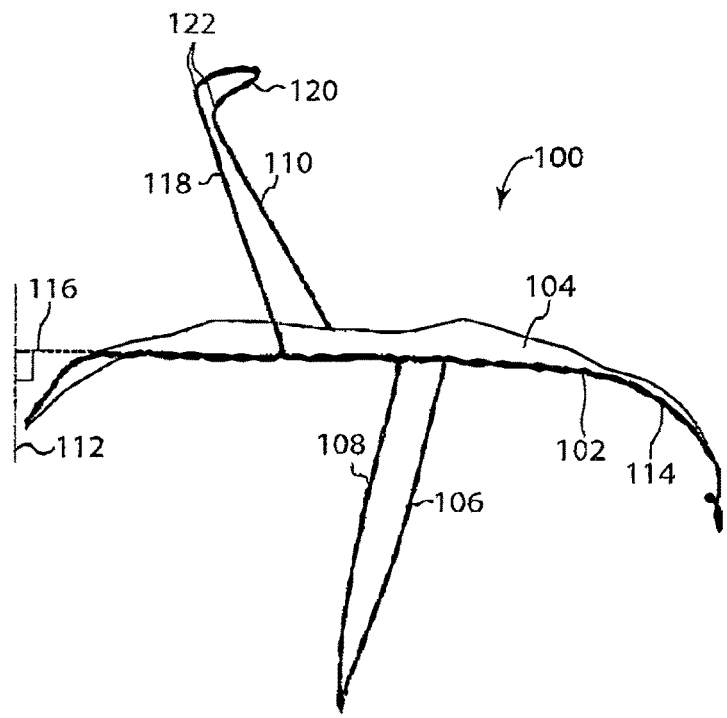
FIG. 1A is a diagram of a side view of an intravascular device. The figure shows exemplary upper and lower stabilizers other than wires.

The present invention relates to intravascular devices, delivery systems, and methods of inhibiting the potentially harmful passage of particulates through the blood stream. Particulates that may be present in blood include, without limitation, blood clots, calcified debris, and emboli. While extremely small particulates may not cause significant harm, passage of larger particulates can result in stroke or other adverse outcomes. The risk of damage resulting from the passage of particulates can increase in association with certain conditions or medical procedures that perturb the vasculature. In order to moderate these risks, the invention features intravascular devices (e.g., with features of intravascular devices described in International Publication Number WO 2012/085916) for preventing particles from passing from a primary blood vessel (e.g., the aorta) to one or more secondary blood vessels (e.g., the left subclavian, left common carotid, or innominate artery). The intravascular device includes an embolic filter, which prevents particles, e.g., emboli, having a dimension greater than 50 µm, in a blood vessel from passing through the filter, and a frame to hold the filter. The frame may be substantially planar and typically has a length between about 80 mm and 90 mm and a width being from about 20 mm to 35 mm. The length of the device may be from approximately 80 mm to 90 mm, or otherwise as may be necessary to approximate a distance between an upper wall of an ascending aorta of a subject, upstream of an opening of an innominate artery and at an upper wall of a descending aorta of a subject downstream of an opening of a left subclavian artery. The width of the device may be from 20 mm to 35 mm or otherwise as may approximate an internal diameter of an aorta of a subject.

The frame may define the shape of the filter, which is attached to the frame, and is typically suitable to be held in contact with both an ascending and a descending aorta. The device also includes at least one upper stabilizer that extends upward from or parallel to the horizontal plane of the filter and may be suitable to contact a medial surface of an innominate artery. The device includes at least one lower stabilizer that extends downward from or parallel to the horizontal plane of the filter and may be suitable to contact a medial surface of the internal wall of the aorta, e.g., opposite the orifices of the branch arteries (e.g., the left subclavian, left common carotid, or innominate artery). One of the upper or lower stabilizers includes a wire connected to the frame and/or filter and extending along the horizontal plane of the filter.

The filter, frame, upper stabilizer(s), lower stabilizer(s), and wire of the device are capable of collapse along a longitudinal axis for ease of delivery to the treatment site. Once deployed in the aortic arch, the lower stabilizer of the device may function to provide lift to the intravascular device in the aortic arch to cover the openings of the branch arteries. Upon installation in the aortic arch, the upper stabilizer may contact the internal wall of the innominate artery to anchor the device in place against blood flow in the aorta, prevent the roll of the device within the aorta, and/or prevent the lift of the device beyond a desired distance from an entry point into the innominate artery of the aorta.

In some embodiments, the wire of the device includes a tether. The tether of the device may be made of a polymeric material, metal, or a combination thereof. The tether may be a solid rod or a hollow tube having a lumen, and the diameter of the tether may be less than about 2 mm (e.g., 1.5 mm, 1.0 mm, 0.5 mm, or 0.25 mm). The tether may have one or more lumens (e.g., 1, 2, or 3 lumens). The lumens of the tether may or may not extend along the length of the tether. In certain embodiments, the tether includes a lumen for attachment of the intravascular device that extends continuously along the tether's length and/or a lumen for a guide wire that is located at the distal end, e.g., below any lumen for attachment, and does not extend the length of the tether. A wire for attachment to the intravascular device or being integral therewith may substantially fill a lumen for attachment in a tether. In some embodiments, the tether of the device includes a guide wire that has a diameter less than the diameter of a lumen of the tether and is configured to pass through a lumen of the tether. A lumen for a guide wire located at the distal end may have a length of 70-160 mm in certain embodiments (e.g., 70 mm, 80 mm, 90 mm, 100 mm, 110 mm, 120 mm, 130 mm, 140 mm, 150 mm, or 160 mm). Preferably, any lumen for a guide wire is longer than the intravascular device. For tethers having a lumen for a guide wire located at the distal end, a transverse dimension of the tether is preferably greater at the distal end relative to the proximal end. A tether and/or guide wire may function to advance the intravascular device through a delivery system and further stabilize the device upon deployment into, e.g., the aortic arch. In some embodiments, the tether and/or guide wire are located beneath the horizontal plane of the filter of the device. The tether may include flushing segments consisting of openings along the length of the tether that allow for fluids, e.g., saline, to pass through the openings when pressure is applied to the proximal end of the tether.

The tether may be additionally attached to a protected lip at, e.g., its distal end, that permits the advancement of the intravascular device through a blood vessel by, e.g., widening the vessel, without causing damage to the vessel wall. The protected lip may be a dilator tip, e.g., that is inflatable, that is configured to expand the blood vessel during insertion, installation, and/or retraction of the device. The dilator tip may have a diameter smaller than the opening of an introducer sheath, and protrude outside the distal end of an introducer sheath to, e.g., expand the opening of a vessel for advancing of an introducer sheath. In devices with, e.g., a dilator tip, at the distal end, the tether may function to inflate the dilator tip by transferring a fluid, e.g., air or saline, from a proximal end to a distal end.

The tether and the dilator tip may have equal rigidity. In other embodiments, the tether is more rigid than the dilator tip, or the tether may be less rigid than the dilator tip, which produces variable rigidity in the device.

The lower stabilizer(s) of the device may be attached to the frame (or be integral with the frame) or may be formed by a wire, e.g., a tether, of the device that extends below the plane of, and along the length of the intravascular device. In some embodiments, a guide wire passes through the lumen of the tether and extends beneath the horizontal plane of the filter. When deployed in an aortic arch, the bending of the guide wire as it conforms to the shape of the aortic arch exerts force on the internal wall of the lumen of the tether. The force is transferred from the tether to the frame and filter of the device to provide lift within the aortic arch. Additionally, a dilator tip and/or an attached tether may be expanded to a desired rigidity that may provide lift as a lower stabilizer by exerting a force on the device beneath the horizontal plane of the filter. When a lower stabilizer includes a tether of the device, the tether passes beneath the plane of the filter to extend along the length of the frame and beyond the distal end of the frame of the device. The tether, when used as a lower stabilizer, may contact a medial surface of the wall of the aorta, e.g., opposite the orifices of the branch arteries.

The wire, e.g., a tether, may also function as an upper stabilizer of the device and exert a force on the proximal end of the frame and filter of the device pushing the distal end of the device in the direction of an ascending aorta to, e.g., prevent the roll of the device and/or limit the lift of the device, by contacting a medial surface of an ascending aorta. When the device includes, e.g., a dilator tip, the dilator tip may have a size and shape to contact the wall of the innominate artery and prevents further lift of the device by anchoring the device in the innominate artery. In embodiments with a dilator tip as an upper stabilizer, a guide wire enclosed within the lumen of the tether may exert a force on the device in the direction of the ascending aorta to position the dilator tip in the opening of the innominate artery. The tether of the device, when functioning as an upper stabilizer, may pass below the horizontal plane of the proximal end of the filter, transect a horizontal plane of the filter at, e.g., a midpoint, and extend above the horizontal plane of the distal end of the filter. The tether may be passed through the filter, and extend parallel or perpendicular to the horizontal plane of the filter.

Any of the frames, upper stabilizer, and/or lower stabilizers of the devices can be fabricated in whole or in part from, e.g., Nitinol or metal wire, superelastic or shape memory alloy material, readily malleable material, or polymer, e.g., nylon. The metal wire may include, e.g., tantalum or platinum. The filters of the intra-vascular device of the invention can include a mesh (e.g., a mesh fabricated with Nitinol or metal wire, nylon, or a combination of both) or perforated film. In devices where a mesh is present, the filter can be rectilinear (e.g., square) or rhomboid. In devices where the pores of the filter are rectilinear or rhomboid, one or both lateral dimensions of the pore can be between 50 and 1000 microns (e.g., 100, 200, 300, 400, 500, 600, or more microns). When a perforated film is present, the pores formed in the perforated film include a varied or unvaried shape, have a varied or constant density across the film, and/or have a constant or varied size. The size of the pores of the filter allows the passage of blood cells (e.g., red blood cells (erythrocytes), white blood cells (leukocytes), and/or platelets (thrombocytes)) and plasma, while being impermeable to particles, e.g., emboli, larger than the pore dimensions. Particles, e.g., emboli, filtered by the mesh of the filter of the present invention are typically particles larger in one or more dimensions than an aperture of the mesh of the filter. Particles, e.g., emboli, filtered by the intra-vascular device of the present invention may be sized to have a dimension greater than 50 µm, e.g., 50 µm, 60 µm, 70 µm, 80 µm, 90 µm, 100 µm, 200 µm, 300 µm, 400 µm, 500 µm, or 1000 µm or more.

In certain instances, a device may require one or more modifications to facilitate one or more methods of tracking the progress of all or a portion of the device. In particular embodiments, one or more radiopaque elements are attached to, included in, or integrated with the device. For example, portions of the frame or filter can be constructed out of Drawn Filled Tubing (DFT wire). Such wire can contain, e.g., a core of tantalum and/or platinum and an outer material of, e.g., Nitinol. In certain embodiments, the DFT wire can be incorporated into all or a portion of the intravascular device frame, stabilizers, or filter. In embodiments where radiopaque wire (e.g., DFT wire) is used in the filter, it can be used throughout the filter or in a certain subset of the filter.

In particular embodiments, including some in which multiple radiopaque elements are attached to, included in, or integrated with a device, it is possible to detect both the progress and particular orientation of all or a portion of a device. In still more particular embodiments, a plurality of radiopaque elements are attached to, included in, or integrated with the filter in a manner that is irregular in two or three dimensions of one or more conformations of the filter, such that the location, orientation, and/or conformation of the filter is indicated upon detection of the radiopaque elements.

The device may further be compatible with common delivery methods used in interventional cardiology (e.g., transcatheter aortic valve implantation (TAVI) procedures). The device may be integrated into a delivery system to enable insertion, installation, and/or retrieval of the device. The delivery system of the invention also features an introducer sheath, e.g., connected to a Y-connector, to facilitate introduction of the intravascular device into the sheath in conjunction with, e.g., a guide wire, e.g., a pigtail catheter.

The introducer sheath may be made of a braided or coiled material or a polymeric material such as, silicone rubber, Nitinol, nylon, polyurethane, and polyethylene terephthalate (PETE) latex. The introducer sheath may have one or more lumens for, e.g., a tether, an intravascular device, and/or a pigtail catheter. The insertion of an intravascular device including a tether along with a pigtail catheter into the introducer sheath is facilitated by a Y-connector, which has three distinct entry ports sized and shaped for mating with an opening at the proximal end of the introducer sheath. In some embodiments, the delivery system of the invention includes an intravascular device, a tether, a protected lip, an introducer sheath, and a Y-connector. In another embodiment, the delivery system includes a tether having flushing segments such that flushing of the introducer sheath and/or the Y-connector is achieved by introducing a flushing agent (e.g., saline) through the tether. The delivery system may include a tether having a lumen for attachment of the intravascular device, e.g., extending the length of the tether, and/or a lumen for a guide wire, e.g., located at the distal end of the tether and not extending its length. A second lumen of a multiple lumen tether may extend continuously along the length of a multiple lumen tether. In embodiments where the lumen for the guide wire is located at the distal end of the tether, deployment of the tether preferably results in volume of the sheath being free to introduce other instruments, e.g., a pigtail catheter. A lumen for a guide wire located at the distal end may have a length of 70-160 mm in certain embodiments (e.g., 70 mm, 80 mm, 90 mm, 100 mm, 110 mm, 120 mm, 130 mm, 140 mm, 150 mm, or 160 mm). Preferably, any lumen for a guide wire is longer than the intravascular device. The tether also preferably has a transverse dimension narrower in the proximal regions where the lumen for the guide wire does not extend. The introducer sheath may be of a size in the range of 6 F to 10 F (e.g., 6 F, 7 F, 8 F, 9 F, or 10 F). Additional delivery systems of the invention may include an aspiration device, introduced through, e.g., a dual lumen, introducer sheath.

The delivery system may also include a deflector to assist in the deployment and positioning of the intravascular device. The deflector may include, e.g., a frame, or may be frameless and may be made of, e.g., an expandable or spread, material. In embodiments of the delivery system including a deflector, the intravascular device of the invention is positioned at the proximal end of the deflector. The deflector may protrude and deploy from the distal end of an introducer sheath before the device to provide a landing zone for, e.g., the intravascular device, and direct additional devices deployed from an introducer sheath below the filter of the deployed intravascular device.

In various embodiments, it is desirable to track the progress of all or a portion of the device of the present invention or of a treatment apparatus used in conjunction with the device of the present invention. A variety of mechanisms for tracking the progress of all or a portion of a device, e.g., by visualizing progress, are contemplated. Methods of tracking include, without limitation, X-ray, fluoroscopy, ultrasound, echocardiography, MRI (magnetic resonance imaging), direct angioscopy, near infrared angiology, intra-vascular ultrasound, CT (computerized tomography) scan, and/or any other suitable imaging technology.

An additional component of the delivery system of the invention may include a pigtail catheter having a radiopaque material to facilitate tracking the progress of the device and other elements of the delivery system. The pigtail catheter may be of size 6 F or smaller (e.g., 1 F, 2 F, 3 F, 4 F, 5 F, or 6 F). In some embodiments, the pigtail catheter is advanced over a guide wire through an introducer sheath along with an intravascular device. For example, a delivery system may include a tether having lumen for a guide wire located at the distal end of the tether to allow for passage of a guide wire. Following deployment of the device, the vacated volume within an introducer sheath lumen allows for passage of additional tools and/or devices, e.g., a pigtail catheter, through the delivery system. In other embodiments, the pigtail catheter is advanced over a guide wire in a first lumen of an introducer sheath, while an intravascular device is advanced through a second lumen of a dual lumen introducer sheath. Once the introducer sheath reaches the desired location, e.g., the aortic arch, the intravascular device is deployed through the first lumen of the introducer sheath. Subsequently, the introducer sheath is rotated, and the pigtail catheter is advanced over a guide wire and deployed beneath the deployed device.

The invention also features methods of use of the intravascular devices and delivery systems of the invention. The devices of the invention are inserted into a vessel, e.g., an aortic arch, of a subject by a delivery system of the invention. The device may be introduced into a blood vessel of a subject in a collapsed form and contained within an introducer sheath. The device may be loaded into the introducer sheath through a Y-connector attached to the proximal end of the introducer sheath. The guide wire of the device may be inserted into the introducer sheath through a first port of the Y-connector. The intravascular device may be inserted with or without a tether into a second port of the Y-connector to combine the intravascular device with the guide wire of the device. The guide wire may be utilized to advance the intravascular device via the introducer sheath and to position the intravascular device in the, e.g., aortic arch. A protected lip, e.g., dilator tip, may also be advanced through the introducer sheath, distal to the device to expand the blood vessel, creating space for the advancing introducer sheath. Upon reaching the desired location within the blood vessel of a subject, the introducer sheath may be retracted, enabling the device to assume an extended form upon its release or deployment from the introducer sheath. In its extended form, the upper stabilizer(s), e.g., an attached extension of the frame of the device, a guide wire, a tether, and/or a dilator tip, of the device may contact a medial surface of an innominate artery and anchor the device within the aortic arch. In its extended form, the lower stabilizer(s), e.g., an attached extension of the frame of the device, a guide wire, a tether, and/or a dilator tip, of the device may contact a medial surface of an ascending aorta and provide lift to the device within the aortic arch. In an additional embodiment, a deflector of the delivery system is first deployed from the distal end of the introducer sheath to assist in the secondary deployment and positioning of the device, which is positioned behind the deflector in an introducer sheath. The position of the device in the desired location, such as, e.g., the aortic arch, can be adjusted by the guide wire and/or tether. The device may include a lumen for a guide wire, e.g., located at the distal end, over which the intravascular device is deployed. A lumen for a guide wire located at the distal end may have a length of 70-160 mm in certain embodiments (e.g., 70 mm, 80 mm, 90 mm, 100 mm, 110 mm, 120 mm, 130 mm, 140 mm, 150 mm, or 160 mm). Preferably, any lumen for a guide wire is longer than the intravascular device. For tethers having a lumen for a guide wire located at the distal end, a transverse dimension of the tether is preferably greater at the distal end relative to the proximal end. In the deployed configuration, the filter attached to the frame and the upper and lower stabilizers may be extended so that the filter assumes a position approximately midway between an upper wall of the aortic arch and a lower wall of the aortic arch, and extends over the distance between the branch arteries of the aorta. A pigtail catheter may also be loaded through the third port of a Y-connector of the introducer sheath to enable visualization and positioning of the device. The pigtail catheter may be passed through space vacated by the portion housing a lumen for a guide wire located at the distal end of the tether following deployment of the intravascular device. The pigtail catheter may be inserted over a second guide wire, which can be subsequently retracted through the introducer sheath when the pigtail catheter is deployed. The positioned device filters particulate, e.g., embolic, material from entering the branch arteries of the aorta. The device and delivery system may be introduced via any suitable vessel, e.g., a peripheral vessel such as the femoral artery.

In one embodiment, a device according to an embodiment of the present invention can be used for protection of the brain from particles, e.g., emboli, prior to, during, and/or after an invasive intracardiac procedure, such as balloon aortic valvuloplasty, balloon mitral valvuloplasty, electrophysiological studies, with or without ablation of ectopic rhythmic sites, insertion of automatic defibrillators, percutaneous valve repair or replacement, or other procedures. Embodiments of the device can be used, for example, in subjects with severe aortic atheroma for brain protection during routine heart catheterization, or for endovascular "cleaning" of atheromatous or thrombotic material. Such an embodiment could be used in subjects with high risk or propensity to form intracardiac clots, for example subjects with hematological disease, arrhythmia of the heart, artificial heart subjects, assist-device subjects, mechanical valve replacement subjects, subjects following intracardiac repair of a pathology, or subjects with congenital heart disease such as patent foramen ovale, and so forth. Other applications of blood particulate filters, medical procedures that benefit from the use of blood particulate filters, and patients at risk of damage resulting from blood particulates are known in the art.

A device according to an embodiment of the present invention can be used, for example, temporarily for acute conditions. For example, the device may be inserted temporarily to protect against cardioembolic stroke or embolic stroke. The device of the present invention may be used to reduce the risk of damage resulting from blood particulates, such as emboli in subjects from suffering conditions associated with an elevated risk thereof, such as acute myocardial infarction (AMI). Thus, in further embodiments, the device may be inserted for the duration of a procedure or treatment. One particular use or outcome of the use of many embodiments of the present invention includes the prevention of particulates from reaching the brain.

The invention also features catheters having a lumen for a guide wire located at the distal end and not extending the length of the catheter. The catheters are similar to tethers of the invention but are not required to be used in conjunction with an intravascular device of the invention, and the description of tethers provided herein is fully applicable to catheters of the invention. The catheter may be attached to any tool for use intravascularly, e.g., an intravascular device for filtering emboli, or may include a mechanism for attachment, e.g., a clasp, a loop, a hook, or a screw thread, to such a tool. A catheter may also include a lumen extending the length of the catheter, e.g., for introduction or removal of a fluid or for insertion, removal, or movement of a tool. In particular, the catheter of the invention may be used with intravascular devices that filter emboli such as those described in U.S. Pat. No. 7,232,453, US 2008/0255603, U.S. Pat. No. 8,062,324, US 2014/0074152, US 2014/0336695, US 2015/0039016, WO 2014/061013, WO 2014/188410, and WO 2014/199381. In some embodiments, the intravascular device may include a filter to prevent a particle in a blood vessel from passing through the filter, a frame to hold the filter, and more than one bow extending outwards from a horizontal plane of the device, such that a lateral surface of the lower of the more than one bow is in contact with a surface of a first blood vessel, e.g., a lateral surface of an ascending aorta, and a lateral surface of the upper of the more than one bow is in contact with a surface of a second blood vessel, e.g., a medial surface of a subclavean artery, e.g., as described in U.S. Pat. No. 8,062,324. Other tools that may be employed include electrodes, e.g., for sensing or ablation, imaging tools, e.g., ultrasound or optical imaging, cutting tools, and balloons.

A device of the present invention may be used in conjunction with one or more pharmaceutical compositions, such as a drug known to treat endocarditis or blood clots.

Figure 1B:
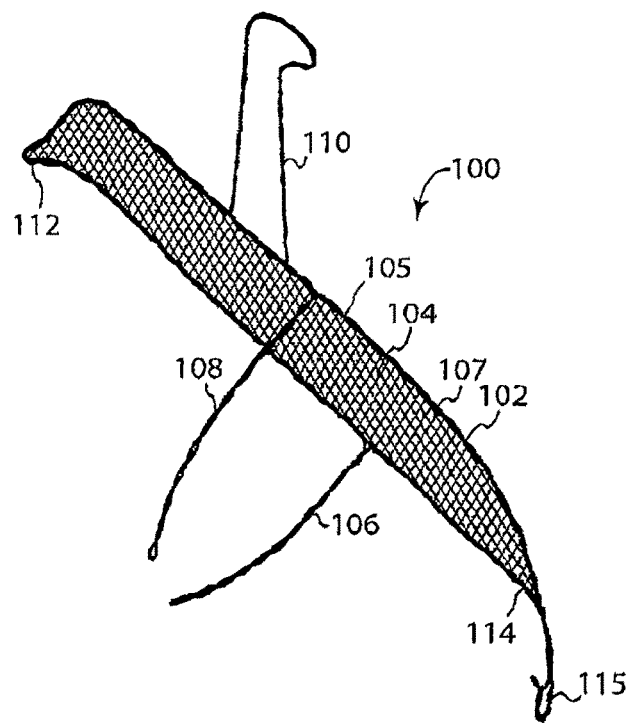
FIG. 1B is a diagram of a three-quarters view of an intravascular device. The figure shows exemplary upper and lower stabilizers other than wires.

Reference is made to FIG. 1A, a schematic diagram of a side-view of an intravascular device, and to FIG. 1B, a three quarters side view of an intravascular device. The devices are depicted without the wire as an upper or lower stabilizer. The frame, filter, upper, and lower stabilizers may be employed in devices having a wire, e.g., tether, as described herein. An intravascular device 100 may include a frame 102, a filter 104, and a series of stabilizers such as lower stabilizers 106 and 108, and an upper stabilizer 110. A first end 112 of device 100, facing upstream of blood flow in an aorta, and a second end 114 of intravascular device 100, facing downstream of blood flow in an aorta, may curve downward below a lateral plane of intravascular device 100. Second end 114 of device 100 may include a hook 115 by which intravascular device 100 may be attached to a tether 205 upon insertion, installation, and/or retraction.

Imaginary line 116 represents a theoretical horizontal plane of intravascular device 100. A lateral plane of intravascular device 100 may include an approximately horizontal line tracing a middle section of frame 102 along intravascular device 100 before the curves of end 112 and end 114.

A first support portion 118 of upper stabilizer 110, as may be proximate to frame 102, may rise away from frame 102 at an angle towards first end 112. A second anchor portion 120 of upper stabilizer 110 may double back on such first support portion at bend 122 and may rise upward and towards a direction of second end 114. Second anchor portion 120 of upper stabilizer 110 may taper in width towards its tip, which may be rounded or flattened.

Filter 104 functions to block or deflect emboli or other particles from entering, for example, the three branch arteries of the aorta (e.g., the innominate artery, the left common carotid artery and the left subclavian artery), while still preserving a space above the filter for blood to swirl and collect at such entries. The space under filter 104 may allow unfiltered blood to pass by the branch arteries of the aorta. Such space in the aorta that is left below the filter means that not all blood passing through the aorta is subject to the filtering or deflecting process of filter 104. Installation in a middle (e.g., between an upper wall of the aortic arch and a lower wall of the aortic arch) of the aorta rather than directly abutting an entry point into the branch arteries may allow a continued flow of blood both through the aorta and into the branch arteries, even if a portion of filter 104 is clogged with embolic or other material.

In some embodiments, lower stabilizer 106 may be connected to frame 102 on a first side (such as a dorsal side), and lower stabilizer 108 may be connected to frame 102 on a second side (such as a ventral side). A first portion of each of lower stabilizer 106 and lower stabilizer 108 that are proximate to frame 102 may extend in substantially parallel lines from frame 102. A second or lower portion of each of lower stabilizers 106 and 108, as are distal to frame 102 may curve towards each other at a point approximating a mid-line of frame 102. The lower ends of lower stabilizers 106 and 108 may terminate in, for example, small loops of the single wound strand that each of the members includes. Such curved endings may prevent a scratching or abrasion of an end of the lower stabilizer 106 or 108 against arterial tissue. The ends of each of lower stabilizers 106 and 108 may in some embodiments touch gently together though they may separate with light pressure.

In some embodiments device 100 may remain positioned in an aorta while a procedure (e.g., TAVI) is undertaken in, for example, a heart, blood vessel, or other in vivo area, where such procedure entails tracing a lead such as a catheter through the aorta. The ease of separation of lower stabilizers 106 and 108 may allow a removal of an arterial catheter or other device from the aorta while intravascular device 100 remains in place, and serves to deflect or filter particulates, e.g., embolic material, away from entering branch arteries of the aorta.

In some embodiments, a tether (205) that may end in, for example, a loop, may be passed through hook 115 so that the hook passes between a contact point of the bend and curve of the loop. When passed through in this manner, a tether 205 fitted with a looped end may be clicked into hook 115, and may securely push device 100 into place or pull device 100 out of position from an aorta. In some embodiments, the hook may end in a ball-tip so that strands from the frame do not fray or scratch the vessel wall or the inner tube of a catheter.

In some embodiments, intravascular device 100 may prevent the passage of, block, divert, or filter-out particles, such as, for example, blood clots, calcified debris or other objects that may block a flow of blood. Frame 102 and intravascular device 100 may also be used to support or keep in place other apparatuses.

In some embodiments, intravascular device 100 may be inserted into a vessel by way of, for example, an introducer sheath, and may be passed into, for example, a blood vessel into which intravascular device 100 may be installed. Other methods of introducing intravascular device 100 into a blood vessel are possible.

In some embodiments, frame 102 may include or be constructed of, for example, Nitinol or other superelastic or shape memory alloy or material. Other materials may be used. In some embodiments, filter 104 may be or include a fine wire netting or mesh, or perforated film, such as a mesh having holes or pores of about 300 microns such that, particles that are larger than the pores or holes are prevented from passing through the filter. Other sizes of holes or eyes may be used. In some embodiments, a shape of filter 104 may be defined or supported by a shape of frame 102.

In some embodiments, one or more of frame 102, upper stabilizer 110 and lower stabilizers 106 and 108 may be fashioned of continuous wire that has different thicknesses or properties in various areas of its lengths. For example, upper stabilizer 110 may be fashioned of a wire or portion of wire that is thin or otherwise highly flexible relative to the thickness or flexibility of one or more of lower stabilizers 106 and 108 or of other portions of frame 102. Such heightened flexibility may enable upper stabilizer 110 and particularly bend 122 and second portion 120 to expand or shrink upon the application of even a small force, such as, for example, the small force exerted by the contact of upper stabilizer 110 with an upper portion of a blood vessel against which it comes into contact. In contrast, lower stabilizers 106 and 108 may be fashioned of a thicker or relatively more rigid wire or filament to provide lift for a mid portion of device 100.

In some embodiments, one or more of the wires that make up upper stabilizer 110 and lower stabilizers 106 and 108 may be wound or braided around frame 102, and no soldered or glued connections between the wound strands of frame 102 and members 110, 106 and 108 may be needed.

Figure 2A:
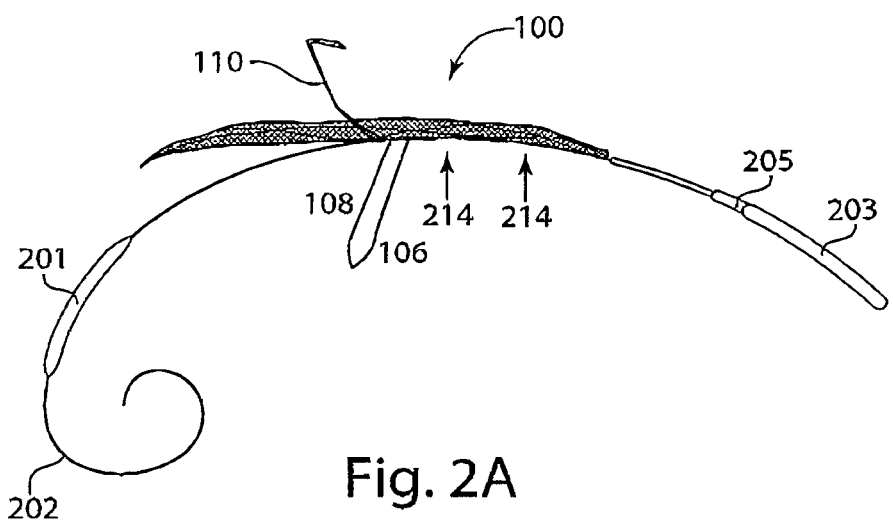
FIGS. 2A-2B are diagrams indicating the force applied to a device by a guide wire.
Figure 2B:
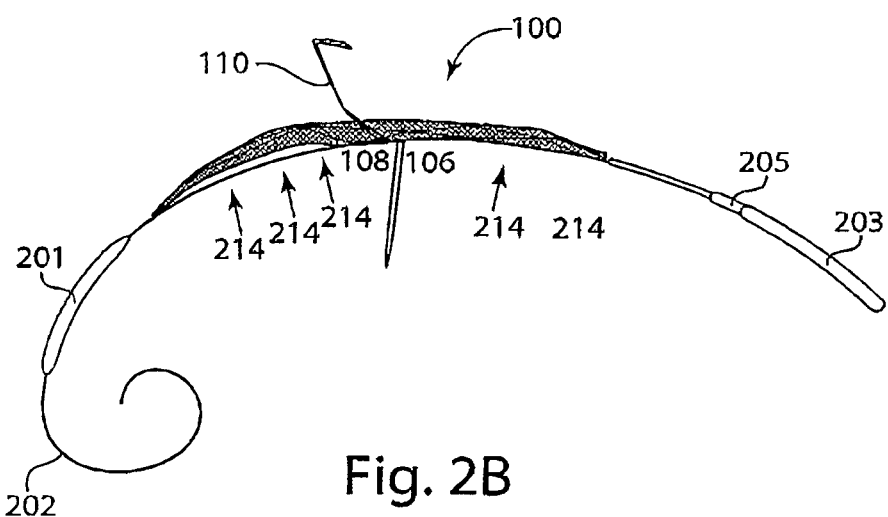

Reference is made to FIGS. 2A-2B, which are schematic diagrams of devices of the invention having a guide wire that exerts a force on a filter and frame of the device. In FIG. 2A, the guide wire 202 is passed through a tether 205 and exerts a mechanical force 214 on a filter 104 and frame 102 of the device 100. The mechanical force 214 exerted by the guide wire 202 on the internal wall of the tether 205 supports the device when deployed. FIG. 2B illustrates that increasing the stiffness of the guide wire 202 increases the mechanical force 214.

Figure 3A:
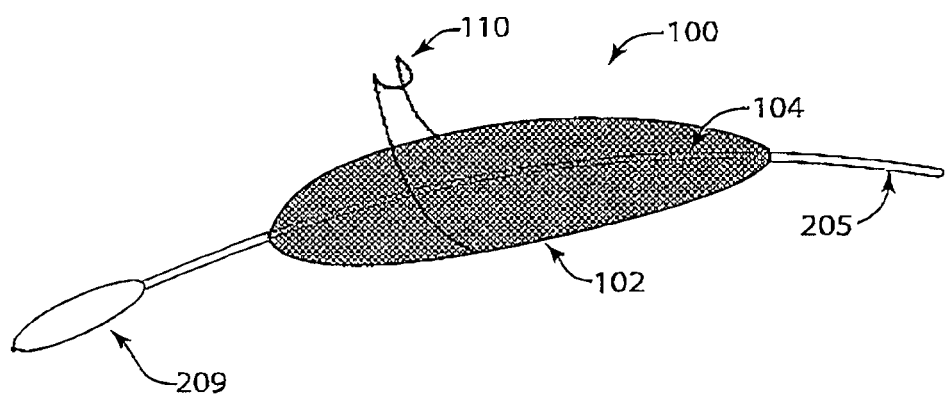
FIGS. 3A-3D are diagrams representing alternative embodiments of an upper or lower stabilizer of the device and the deployment of such devices in an aortic arch.
Figure 3B:
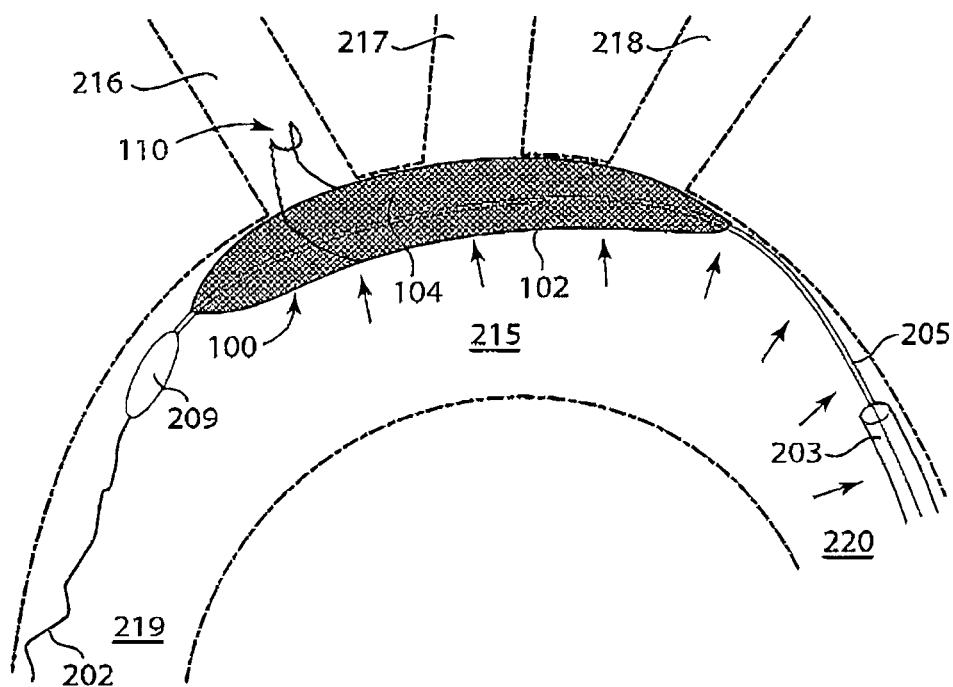

Reference is made to FIGS. 3A-3D, which are schematic drawings of an intravascular device 100 having a tether 205 and a dilator tip 209 as a lower stabilizer or an upper stabilizer. FIG. 3A depicts an embodiment of the device 100 in which a tether 205 attached to a dilator tip 209 is connected to the device 100 beneath the filter 104 along the length of intravascular device 100, which has an upper stabilizer 110 attached. The tether 205 and attached dilator tip 209 support the intravascular device 100 by providing lift beneath the device and act as a lower stabilizer to stabilize the device in, e.g., an aortic arch. FIG. 3B is a representation of the device 100 of FIG. 3A deployed in the aortic arch 215. The device 100 is advanced over the guide wire 202 through the introducer sheath 203 into the aortic arch 215, where the upper stabilizer 110 extends into and contacts the medial surface of an innominate artery 216, and the filter 104 and frame 102 extend across the orifices of the innominate artery 216, the left common carotid artery 217, and the left subclavian artery 218. The tether 205 and dilator tip 209 provide mechanical force 214 on the filter 104 and frame 102 to lift the device 100 as blood passes from the ascending aorta 219 to the descending aorta 220. The lower stabilizers (106, 108) are optional in this embodiment, as the tether 205 and dilator tip 209 function as lower stabilizers of the device 100.

Figure 3C:
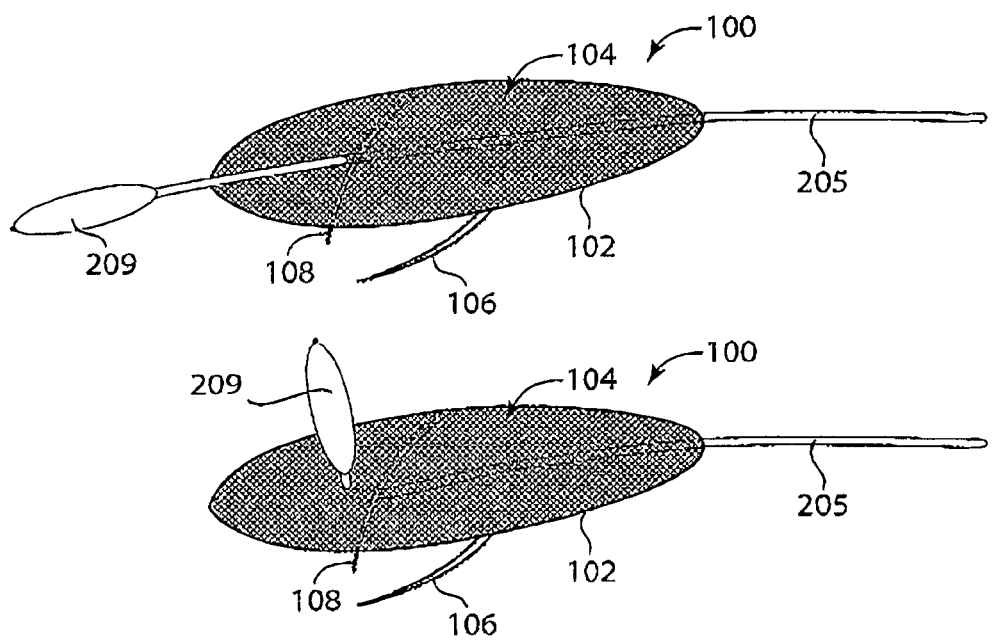
Figure 3D:
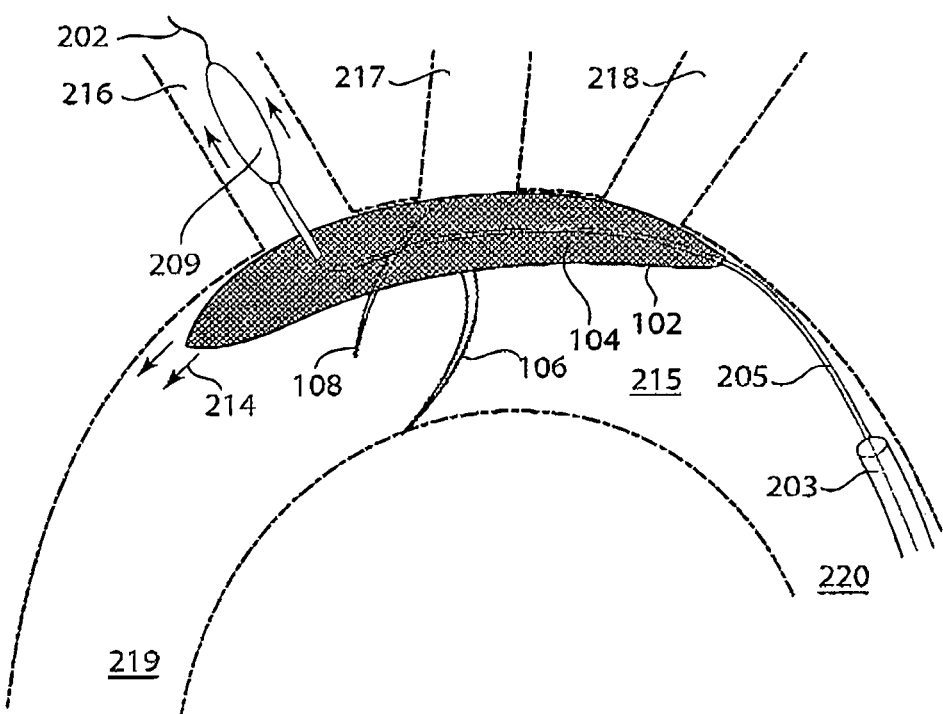

FIG. 3C represents an embodiment of a device of the invention having tether 205 with an attached dilator tip 209 passing through the filter 104 of the intravascular device 100. In the embodiment on the top, the tether 205 functions as the upper stabilizer of the intravascular device 100 to limit the lift of the lower stabilizers 106 and 108. In the embodiment on the bottom, the dilator tip 209 functions as the upper stabilizer of the intravascular device 100 by extending through the filter 104 upwards from the horizontal plane 116 of the filter 104. In FIG. 3D, the lower device 100 of FIG. 3C is deployed in an aortic arch 215. The device 100 is advanced over the guide wire 202 through the introducer sheath 203 into the aortic arch 215, where the dilator tip 209 extends into and contacts the medial surface of an innominate artery 216, and the filter 104 and frame 102 extend across the orifices of the innominate artery 216, the left common carotid artery 217, and the left subclavian artery 218. A guide wire 202 passing through a lumen of tether 205 and exerting a force on the lumen wall of tether 205 provides mechanical forces 214 on the filter 104 and frame 102 of device 100 in the direction of an ascending aorta 219. The dilator tip 209 functions as the upper stabilizer of the device 100 in the innominate artery 216, to limit the lift exerted by the lower stabilizers 106 and 108 of the device 100.

Figure 4:
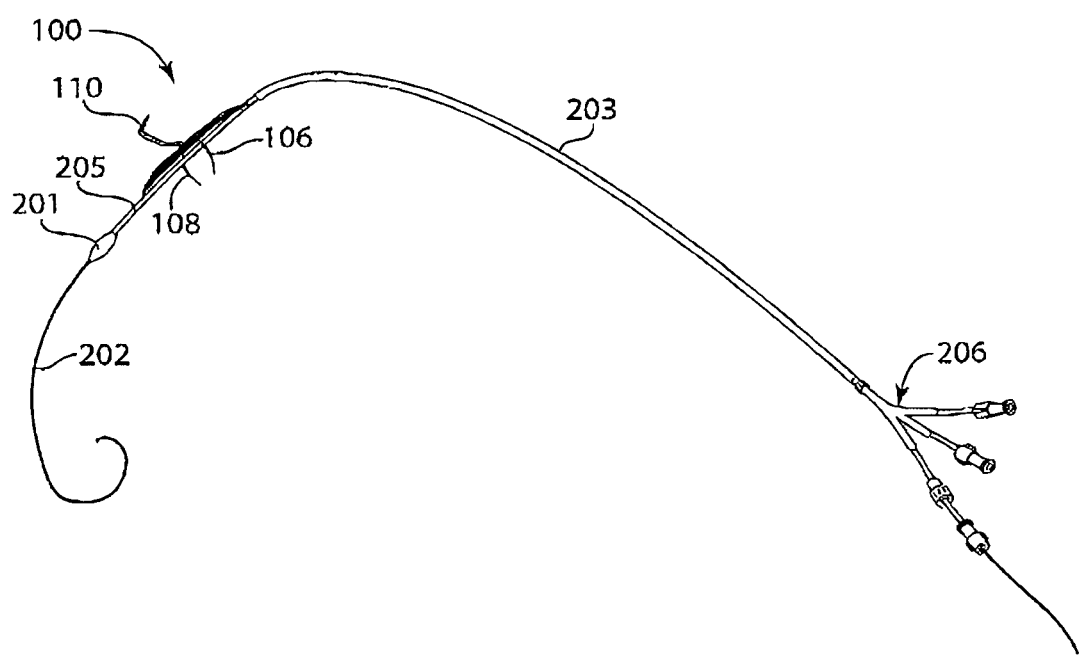
FIG. 4 is a diagram of a delivery system including an intravascular device, Y-connector, tether, sheath, and a protected lip, in accordance with an embodiment of the invention.

Reference is made to FIG. 4, a schematic diagram of a delivery system combining a Y-connector 206 with an introducer sheath 203 for insertion of an intravascular device 100, which an upper stabilizer 110, and lower stabilizers 106 and 108, through a port of the Y-connector. The tether 205 may also be loaded over the guide wire 202 through the Y-connector and have a protected lip 201 that protrudes outside the distal end of the introducer sheath 203.

Reference is made to FIGS. 5A-5B, schematic diagrams of two embodiments of a tether 205 with a dilator tip 209 attached at the distal end. The embodiment of the delivery system depicted in FIG. 5A is a schematic of a low profile tether 205 with a constant rigidity extending along the length of the tether and the dilator tip 209. The dilator tip 209 protrudes out of the distal end of introducer sheath 203, as it is advanced proximal to the intravascular device 100, having a filter 104, a frame 102, an upper stabilizer 110, and lower stabilizers 106 and 108. FIG. 5B is a schematic of tether 205 with a rigidity greater than the rigidity of a dilator tip 209, which is advanced proximal to an intravascular device 100, having an intravascular device 100, an upper stabilizer 110, and lower stabilizers 106 and 108.

Figure 6A:
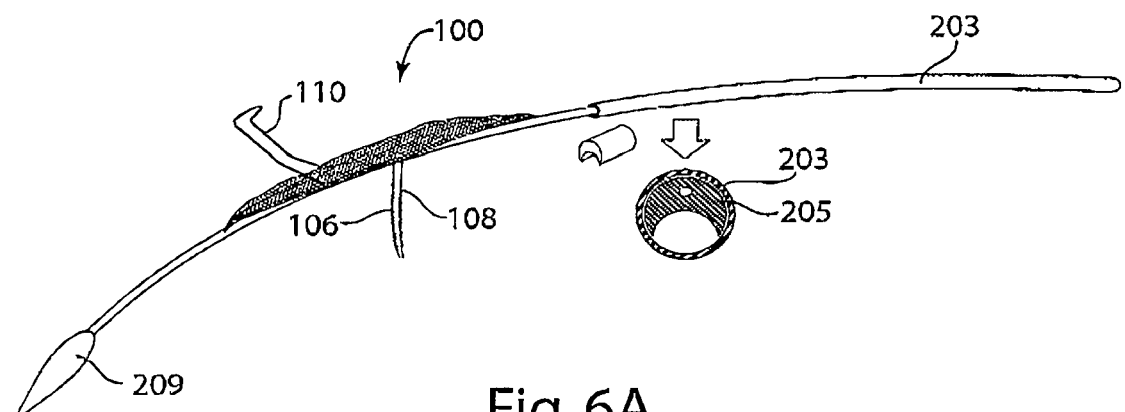
FIG. 6A is a diagram of a delivery system with a single lumen introducer sheath in accordance with an embodiment of the invention. The inset schematic provides a cross-sectional view of the tether positioned in the single lumen introducer sheath.
Figure 6B:
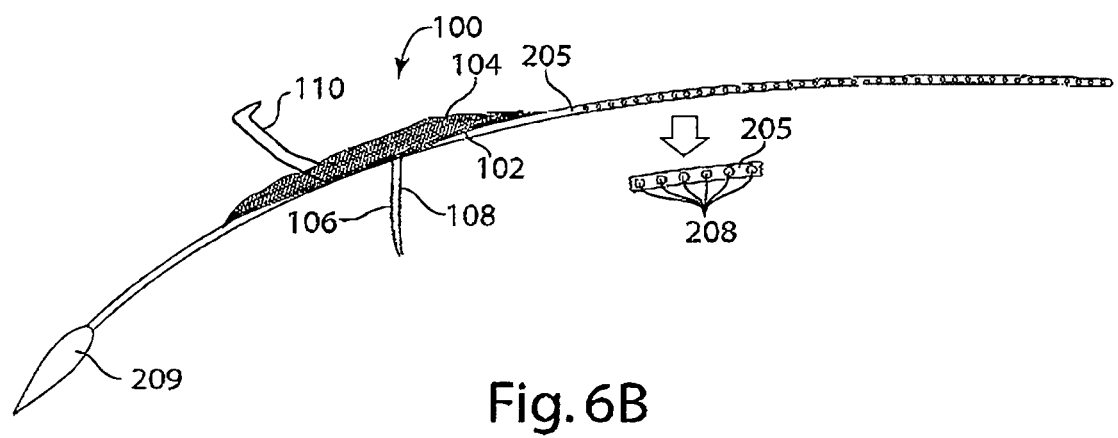
FIG. 6B is a diagram of a delivery system with a tether with flushing segments seen in the inset, in accordance with an embodiment of the invention. The inset schematic provides a magnified view of the flushing segments.

Reference is made to FIGS. 6A-6B, drawings of embodiments of the tether of the delivery system of the invention. In FIG. 6A, an embodiment of a delivery system of the invention is depicted having a device 100 deployed from the distal end of an introducer sheath 203 and tether 205 attached to a dilator tip 209 loaded into a single lumen of the introducer sheath 203. The cross-sectional view of introducer sheath 203 shows tether 205 at the top of the lumen and space remaining for introducing additional devices, e.g., a pigtail catheter 204. FIG. 6B depicts an embodiment of tether 205 having flushing elements 208 through which, e.g., saline, may be extruded to rinse the Y-connector 206 or introducer sheath 203 of the delivery system.

Figure 7:
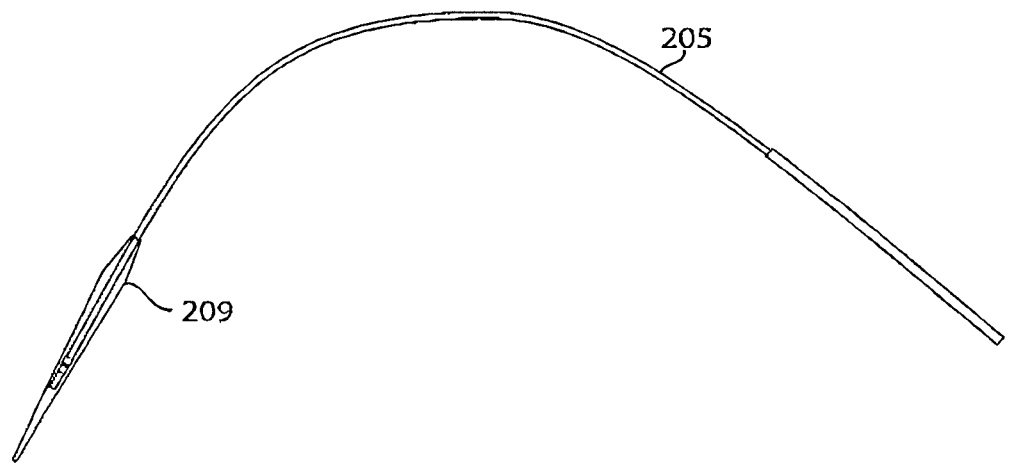
FIG. 7 is a diagram of a tether with an inflatable dilator tip at its distal end.

Reference is made to FIG. 7, a schematic diagram of a tether having an inflatable dilator tip 209 at the distal end.

Figure 8:
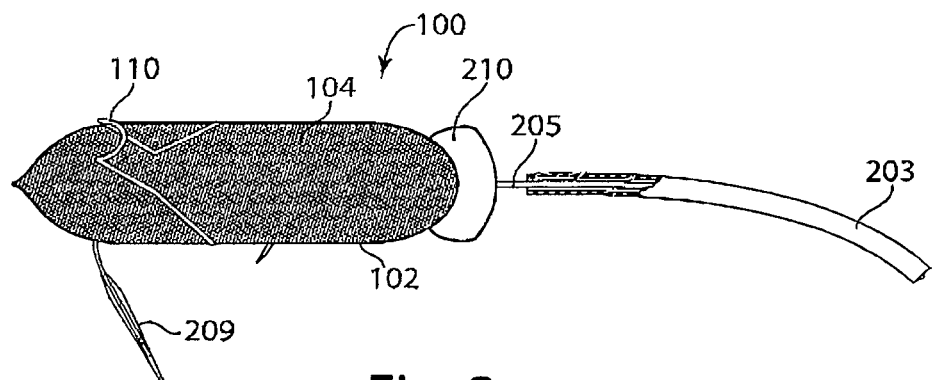
FIG. 8 is a diagram of a delivery system of an intravascular device with a deflector, in accordance with an embodiment of the invention.

Reference is made to FIG. 8, a schematic diagram of a delivery system of the invention that includes a deflector. A tether 205 attached to a dilator tip 209 is enclosed by an introducer sheath 203. A deflector 210 is first deployed from a distal end of an introducer sheath 203 and provides a landing zone for the intravascular device 100, which is deployed from an introducer sheath 203 and lands above the horizontal plane of the deflector 210. The deflector 210 directs subsequent deployment of additional devices from the introducer sheath 203 below the horizontal plane of the deflector to prevent entanglement of secondary devices with the intravascular device 100.

Figure 9A:
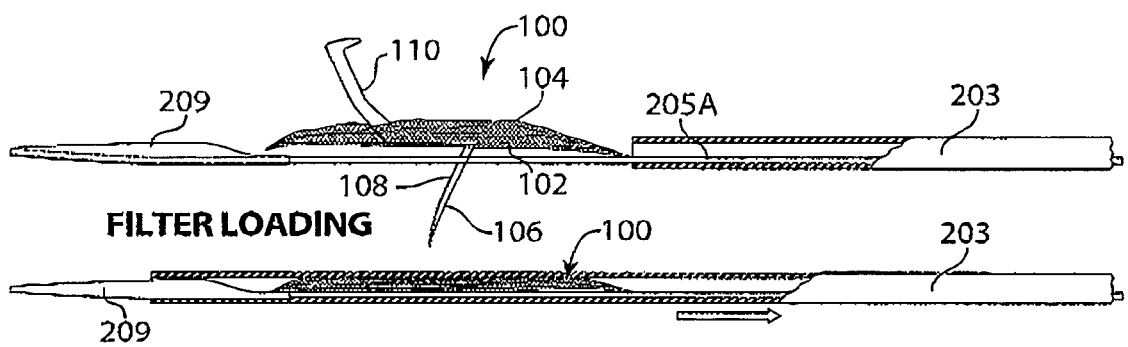
FIG. 9A is a diagram of an intravascular device being loaded into an introducer sheath of a delivery system, in accordance with an embodiment of the invention.
Figure 9B:
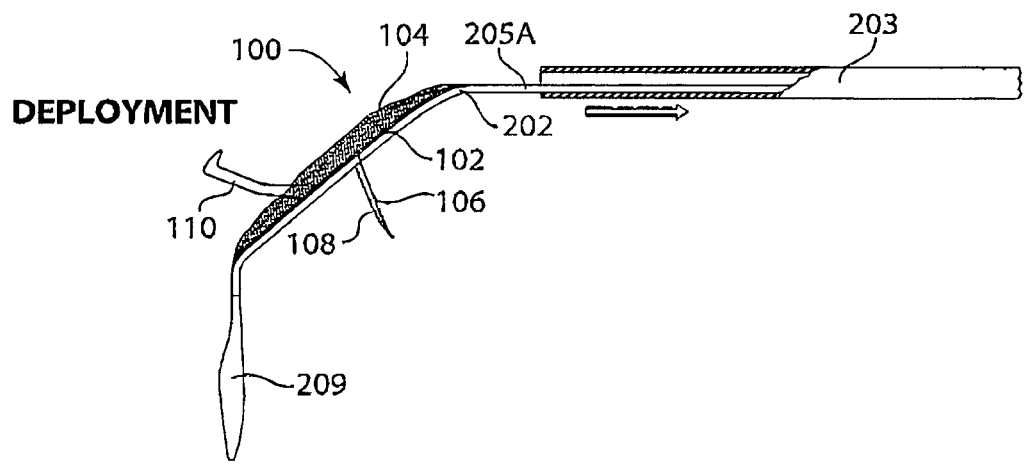
FIG. 9B is a diagram of an intravascular device being deployed by retracting an introducer sheath of a delivery system, in accordance with an embodiment of the invention.

Reference is made to FIGS. 9A-9B, schematic diagrams of the loading and deployment of an intravascular device from an introducer sheath of the invention. In FIG. 9A, tether 205A attached to a dilator tip 209 is advanced through an introducer sheath 203, with a dilator tip 209 protruding from the distal end of the introducer sheath 203. The intravascular device 100 is collapsed along its longitudinal axis when loaded into the introducer sheath 203. FIG. 9B depicts the retraction of an introducer sheath 203 to deploy the intravascular device 100 over a guide wire 202.

Figure 10A:
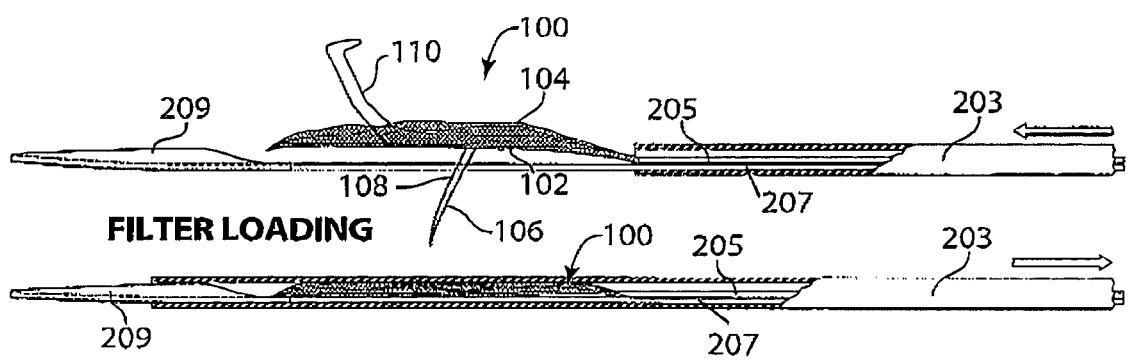
FIG. 10A is a diagram of an intravascular device attached to a first tether being loaded with a second tether connected to a dilator tip into a single lumen of an introducer sheath of a delivery system, in accordance with an embodiment of the invention.
Figure 10B:
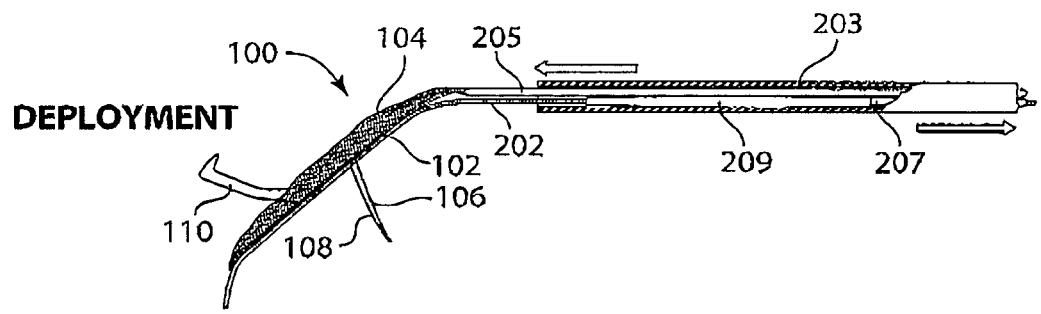
FIG. 10B is a diagram of an intravascular device attached to a first tether being deployed from a single lumen of an introducer sheath by a delivery system, in accordance with an embodiment of the invention.

Reference is made to FIGS. 10A-10B, schematic diagrams of the loading and deployment of an intravascular device 100 attached to a tether 205 in addition to tether 207 with a dilator tip 209. In FIG. 10A, tether 207 attached to a dilator tip 209 is advanced through an introducer sheath 203, with a dilator tip 209 protruding from the distal end of the introducer sheath 203. An intravascular device 100 attached to a tether 205 is collapsed along its longitudinal axis when loaded into an introducer sheath 203. In FIG. 10B, the intravascular device 100 is advanced through the distal end of the introducer sheath 203 by pushing on the attached tether 205. When the introducer sheath 203 and tether 207 attached to dilator tip 209 are retracted in the direction opposite of the advancing tether 205, the intravascular device 100 is deployed from the distal end of introducer sheath 203.

Figure 11:
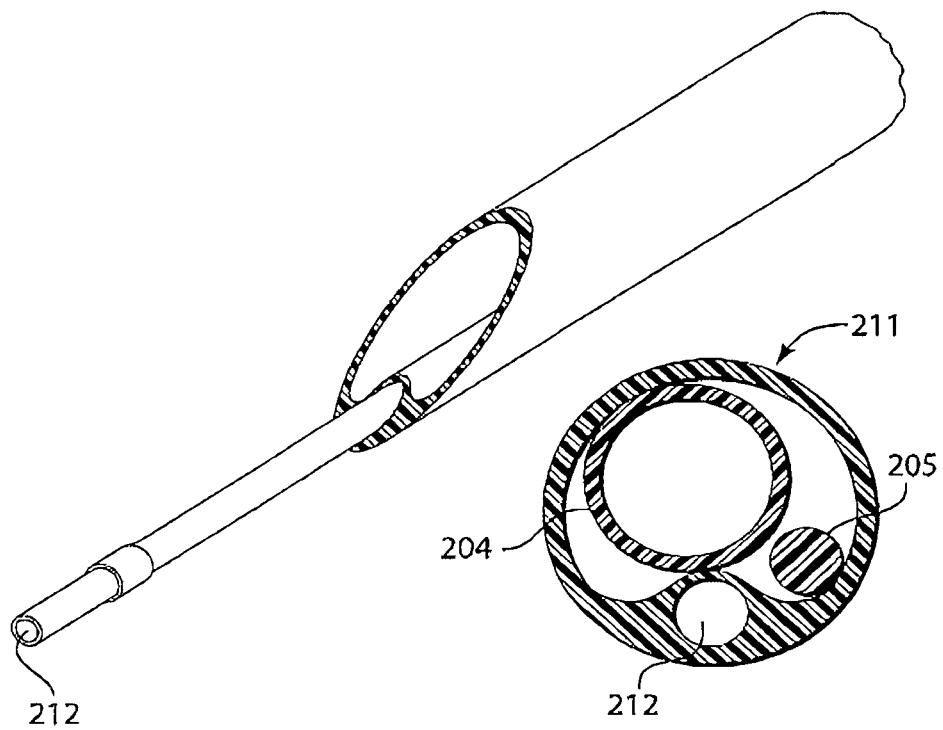
FIG. 11 is a diagram of a dual-lumen introducer sheath of a delivery system with an aspirator, in accordance with an embodiment of the invention.

Reference is made to FIG. 11, a schematic diagram of a dual lumen introducer sheath. In a dual lumen introducer sheath 211 of the invention, a first lumen with a diameter larger than that of a second lumen is provided to advance a pigtail catheter 204 through a first lumen and a device 100 and tether 205 through a second lumen, without entangling the two devices. The dual lumen introducer sheath 211 may further enclose an aspirator 212 of the invention for desired indications. In the cross-sectional view, the pigtail catheter 204 is positioned in a first lumen above a second lumen that includes a tether 205 and an aspirator 212.

Figure 12:
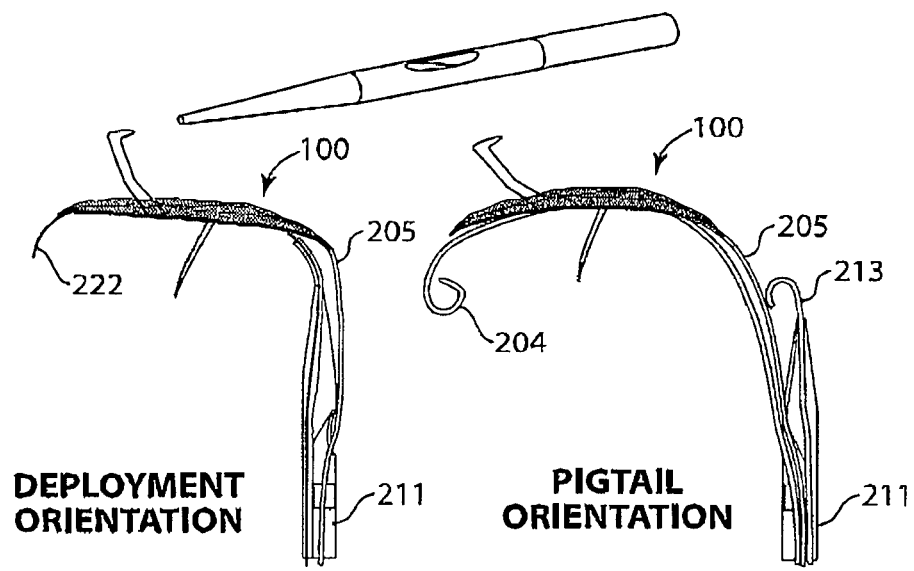
FIG. 12 is a set of diagrams of the orientation of deployment of an intravascular device (left) and the orientation of deployment of a pigtail catheter (right) from a dual lumen introducer sheath of a delivery system.

Reference is made to FIG. 12, a schematic diagram of the orientation of deployment of an intravascular device 100 and pigtail catheter 204 from a dual lumen introducer sheath 211. In the diagram on the left, a second guide wire 222 is advanced through a first lumen of a dual lumen introducer sheath 211 and exits through the distal opening of the first lumen of a dual lumen introducer sheath 211. An intravascular device 100 is advanced by a tether 205 through a second lumen of a dual lumen introducer sheath 211 and deployed above the guide wire 222. In the diagram on the right, the dual lumen introducer sheath 211 is rotated such that a pigtail catheter 204 having a blunted tip 213 is advanced over a guide wire 222 and deployed from a first lumen of a dual lumen introducer sheath 211 beneath the intravascular device 100 while the guide wire 222 is retracted into the first lumen of the dual introducer sheath 211.

Reference is made to FIG. 13, a schematic diagram of a tether having a lumen located at its distal end. In tether 223, a first portion 224, which may include a lumen, extends the length of the tether and provides for attachment to intravascular device 100, shown deployed from an introducer sheath 203. A second portion 225, which includes a lumen for a guide wire, is located at the distal end of tether 223 and does not extend the length of the tether. Portion 225 is located beneath the intravascular device 100 and is attached to a protected lip 201.

Reference is made to FIG. 14, a schematic diagram of the loading of an intravascular device 100 and tether 223, as depicted in FIG. 13, into an introducer sheath 203. When the tether and device are loaded into the sheath, protected lip 201 extends outside of the distal end of the sheath. The sheath, tether, and device may be advanced over guide wire 202 via the lumen in portion 225.

It will be appreciated by persons skilled in the art that embodiments of the invention are not limited by what has been particularly shown and described hereinabove. Rather the scope of at least one embodiment of the invention is defined by the claims below.

The invention claimed is:

1. An intravascular device for deflecting emboli comprising:
   a. a frame having a length;
   b. an embolic filter attached to and extending the length of said frame; and
   wherein the device comprises a tether configured to run along a horizontal plane of the filter and exert a force on the frame and/or the filter when deployed in an aortic arch of a subject to hold the filter against an opening of at least one of an innominate artery, a left carotid artery and a left subclavian artery;

wherein said tether runs along said length of said filter from a proximal portion to a distal portion and said tether extends further than a distal end of the frame;

wherein said tether comprises at least one lumen; and wherein a guide wire is positioned within said lumen and is configured to exert said force on an inner wall of said lumen of said tether; and wherein said tether comprises a dilator tip.

2. The device of claim 1, wherein said frame defines a shape of said filter and said frame is suitable to be held in contact with both an ascending and a descending aorta.

3. The device of claim 1, wherein said tether is configured to exert said force downward from said horizontal plane of said filter.

4. The device of claim 1, wherein said tether is configured to exert said force upward from said horizontal plane of said filter.

5. The device of claim 1, wherein said tether comprises an attached protected lip.

6. The device of claim 1, wherein said tether is configured to exert said force below or above said horizontal plane of said filter.

* * * * *